(12) United States Patent
Kim et al.

(10) Patent No.: US 8,372,119 B2
(45) Date of Patent: Feb. 12, 2013

(54) DUAL ROD CROSS CONNECTORS AND INSERTER TOOLS

(75) Inventors: Daniel Huan Kim, Mountain View, CA (US); Michael Carl Michielli, Medway, MA (US)

(73) Assignee: DePuy Spine, Inc., Raynham, MA (US)

( * ) Notice: Subject to any disclaimer, the term of this patent is extended or adjusted under 35 U.S.C. 154(b) by 966 days.

(21) Appl. No.: 12/248,389

(22) Filed: Oct. 9, 2008

(65) Prior Publication Data

US 2009/0036928 A1    Feb. 5, 2009

Related U.S. Application Data

(63) Continuation of application No. 10/929,095, filed on Aug. 27, 2004, now Pat. No. 7,717,938.

(51) Int. Cl.
*A61B 17/70* (2006.01)

(52) U.S. Cl. ....................................................... 606/250

(58) Field of Classification Search .................. 606/246, 606/250–253, 257, 260
See application file for complete search history.

(56) References Cited

U.S. PATENT DOCUMENTS

| | | | |
|---|---|---|---|
| 180,881 A | 8/1876 | Howson |
| 457,964 A | 8/1891 | Bolte |
| 483,342 A | 9/1892 | Bolte |
| 596,729 A | 1/1898 | White |
| 900,717 A | 10/1908 | Feaster |
| 1,455,441 A | 5/1923 | Hodny |
| 2,638,301 A | 5/1953 | Smith |
| 3,012,091 A | 12/1961 | Schiffmann |
| 3,019,504 A | 2/1962 | Castagliuolo |
| 3,499,222 A | 3/1970 | Linkow |
| 3,752,203 A | 8/1973 | Hill, Jr. |
| 4,011,602 A | 3/1977 | Rybicki et al. |
| 4,085,744 A | 4/1978 | Lewis et al. |
| 4,179,905 A | 12/1979 | Schultenkamper |
| 4,289,124 A | 9/1981 | Zickel |
| 4,404,967 A | 9/1983 | Bacal et al. |
| 4,411,259 A | 10/1983 | Drummond |
| 4,611,580 A | 9/1986 | Wu |
| 4,611,581 A | 9/1986 | Steffee |

(Continued)

FOREIGN PATENT DOCUMENTS

| | | |
|---|---|---|
| DE | 867422 | 2/1953 |
| DE | 3219575 | 12/1983 |

(Continued)

OTHER PUBLICATIONS

Asher, et al., "A Modular Spinal Rod Linkage System to Provide Rotational Stability", SPINE, vol. 13, No. 3, pp. 272-277, 1998.

(Continued)

*Primary Examiner* — Kevin T Truong
*Assistant Examiner* — Michael Araj
(74) *Attorney, Agent, or Firm* — Nutter McClennen & Fish LLP

(57) ABSTRACT

An implantable spinal cross connector is provided for connecting one or more spinal fixation devices, and more preferably for connecting two spinal fixation rods that are implanted within a patient's spinal system. In general, an exemplary cross connector in accordance with the present invention includes an elongate body with at least one rod-receiving recess formed therein, and a locking mechanism that is adapted to couple to the elongate body and that is effective to lock a spinal fixation rod within the rod-receiving recess(es). The present invention also provides an inserter tool to facilitate implanting a spinal implant or device, such as a spinal cross connector.

22 Claims, 9 Drawing Sheets

U.S. PATENT DOCUMENTS

| | | |
|---|---|---|
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,743,260 A | 5/1988 | Burton |
| 4,759,769 A | 7/1988 | Hedman et al. |
| 4,763,644 A | 8/1988 | Webb |
| 4,771,767 A | 9/1988 | Steffee |
| 4,773,402 A | 9/1988 | Asher et al. |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,950,269 A | 8/1990 | Gaines, Jr. |
| 4,957,495 A | 9/1990 | Kluger |
| 5,002,542 A | 3/1991 | Frigg |
| 5,005,562 A | 4/1991 | Cotrel |
| 5,010,879 A | 4/1991 | Moriya et al. |
| 5,024,213 A | 6/1991 | Asher et al. |
| 5,030,220 A | 7/1991 | Howland |
| 5,067,955 A | 11/1991 | Cotrel |
| 5,084,049 A | 1/1992 | Asher et al. |
| 5,092,866 A | 3/1992 | Breard et al. |
| 5,092,893 A | 3/1992 | Smith |
| 5,102,412 A | 4/1992 | Rogozinski |
| 5,113,685 A | 5/1992 | Asher et al. |
| 5,116,334 A | 5/1992 | Cozad et al. |
| 5,120,171 A | 6/1992 | Lasner |
| 5,127,912 A | 7/1992 | Ray et al. |
| 5,129,899 A | 7/1992 | Small et al. |
| 5,129,900 A | 7/1992 | Asher et al. |
| 5,133,716 A | 7/1992 | Plaza |
| 5,147,359 A | 9/1992 | Cozad et al. |
| 5,147,360 A | 9/1992 | Dubousset |
| 5,154,718 A | 10/1992 | Cozad et al. |
| 5,176,678 A | 1/1993 | Tsou |
| 5,176,680 A | 1/1993 | Vignaud et al. |
| 5,190,543 A | 3/1993 | Schlapfer |
| 5,207,678 A | 5/1993 | Harms et al. |
| 5,234,431 A | 8/1993 | Keller |
| 5,242,443 A | 9/1993 | Kambin |
| 5,261,907 A | 11/1993 | Vignaud et al. |
| 5,261,913 A | 11/1993 | Marnay |
| 5,275,600 A | 1/1994 | Allard et al. |
| 5,282,801 A | 2/1994 | Sherman |
| 5,282,863 A | 2/1994 | Burton |
| 5,304,177 A | 4/1994 | Pennig |
| 5,306,275 A | 4/1994 | Bryan |
| 5,312,405 A | 5/1994 | Korotko et al. |
| 5,330,473 A | 7/1994 | Howland |
| 5,334,203 A | 8/1994 | Wagner |
| 5,360,431 A | 11/1994 | Puno et al. |
| 5,366,455 A | 11/1994 | Dove et al. |
| 5,368,594 A | 11/1994 | Martin et al. |
| 5,387,213 A | 2/1995 | Breard et al. |
| 5,395,370 A | 3/1995 | Muller et al. |
| 5,397,363 A | 3/1995 | Gelbard |
| 5,403,316 A | 4/1995 | Ashman |
| 5,415,661 A | 5/1995 | Holmes |
| 5,419,522 A | 5/1995 | Luecke et al. |
| 5,423,818 A | 6/1995 | Van Hoeck et al. |
| 5,437,671 A | 8/1995 | Lozier et al. |
| 5,439,463 A | 8/1995 | Lin |
| 5,454,812 A | 10/1995 | Lin |
| 5,458,642 A | 10/1995 | Beer et al. |
| 5,470,333 A | 11/1995 | Ray |
| 5,474,086 A | 12/1995 | McCormick et al. |
| 5,476,462 A | 12/1995 | Allard et al. |
| 5,487,742 A | 1/1996 | Cotrel |
| 5,496,321 A | 3/1996 | Puno et al. |
| 5,498,263 A | 3/1996 | DiNello et al. |
| 5,514,132 A | 5/1996 | Csernatony et al. |
| 5,522,816 A | 6/1996 | Dinello et al. |
| 5,527,314 A | 6/1996 | Brumfield et al. |
| 5,531,745 A | 7/1996 | Ray |
| 5,534,002 A | 7/1996 | Brumfield et al. |
| 5,540,688 A | 7/1996 | Navas |
| 5,549,607 A | 8/1996 | Olson et al. |
| 5,556,431 A | 9/1996 | Buttner-Janz |
| 5,562,662 A | 10/1996 | Brumfield et al. |
| 5,562,663 A | 10/1996 | Wisnewski et al. |
| 5,562,737 A | 10/1996 | Graf |
| 5,571,191 A | 11/1996 | Fitz |
| 5,582,612 A | 12/1996 | Lin |
| 5,584,831 A | 12/1996 | McKay |
| 5,586,983 A | 12/1996 | Sanders et al. |
| 5,591,165 A | 1/1997 | Jackson |
| 5,601,552 A | 2/1997 | Cotrel |
| 5,609,592 A | 3/1997 | Brumfield et al. |
| 5,616,142 A | 4/1997 | Yuan et al. |
| 5,620,444 A | 4/1997 | Assaker |
| 5,624,442 A | 4/1997 | Mellinger et al. |
| 5,630,816 A | 5/1997 | Kambin |
| 5,651,789 A | 7/1997 | Cotrel |
| 5,662,653 A | 9/1997 | Hattori et al. |
| 5,667,506 A | 9/1997 | Sutterlin |
| 5,667,507 A | 9/1997 | Corin et al. |
| 5,669,910 A | 9/1997 | Korhonen et al. |
| 5,672,175 A | 9/1997 | Martin |
| 5,676,703 A | 10/1997 | Gelbard |
| 5,683,393 A | 11/1997 | Ralph |
| 5,688,272 A | 11/1997 | Montague et al. |
| 5,700,292 A | 12/1997 | Margulies |
| 5,704,936 A | 1/1998 | Mazel |
| 5,707,372 A | 1/1998 | Errico et al. |
| 5,709,684 A | 1/1998 | Errico et al. |
| 5,709,685 A | 1/1998 | Dombrowski et al. |
| 5,716,355 A | 2/1998 | Jackson et al. |
| 5,743,907 A | 4/1998 | Asher et al. |
| 5,743,911 A | 4/1998 | Cotrel |
| 5,752,955 A | 5/1998 | Errico |
| 5,776,135 A | 7/1998 | Errico et al. |
| 5,876,403 A | 3/1999 | Shitoto |
| 5,885,284 A | 3/1999 | Errico et al. |
| 5,899,903 A | 5/1999 | Cotrel |
| RE36,221 E | 6/1999 | Breard et al. |
| 5,928,232 A | 7/1999 | Howland et al. |
| 5,934,818 A | 8/1999 | Schmitt et al. |
| 5,937,363 A | 8/1999 | Saidi et al. |
| 5,947,966 A | 9/1999 | Drewry et al. |
| 5,961,516 A | 10/1999 | Graf |
| 5,980,521 A | 11/1999 | Montague et al. |
| 5,980,523 A | 11/1999 | Jackson |
| 5,989,250 A | 11/1999 | Wagner et al. |
| 5,989,251 A | 11/1999 | Nichols |
| 6,063,089 A | 5/2000 | Errico et al. |
| RE36,758 E | 6/2000 | Fitz |
| 6,083,226 A | 7/2000 | Fiz |
| 6,110,173 A | 8/2000 | Thomas, Jr. |
| 6,113,600 A | 9/2000 | Drummond et al. |
| 6,126,660 A | 10/2000 | Dietz |
| 6,132,464 A | 10/2000 | Martin |
| 6,136,003 A | 10/2000 | Hoeck et al. |
| 6,139,548 A | 10/2000 | Errico |
| 6,171,311 B1 | 1/2001 | Richelsoph |
| 6,217,578 B1 | 4/2001 | Crozet et al. |
| 6,234,705 B1 | 5/2001 | Troxell |
| 6,238,396 B1 | 5/2001 | Lombardo |
| 6,264,658 B1 | 7/2001 | Lee et al. |
| 6,267,764 B1 | 7/2001 | Elberg |
| 6,273,888 B1 | 8/2001 | Justis |
| 6,283,967 B1 | 9/2001 | Troxell et al. |
| 6,287,309 B1 | 9/2001 | Baccelli et al. |
| 6,302,882 B1 | 10/2001 | Lin et al. |
| 6,315,779 B1 | 11/2001 | Morrison et al. |
| 6,328,741 B1 | 12/2001 | Richelsoph |
| 6,355,038 B1 | 3/2002 | Pisharodi |
| 6,402,751 B1 | 6/2002 | Hoeck et al. |
| 6,413,257 B1 | 7/2002 | Lin et al. |
| 6,413,258 B1* | 7/2002 | Bernhardt, Jr. ............... 606/252 |
| 6,419,703 B1 | 7/2002 | Fallin et al. |
| 6,432,108 B1 | 8/2002 | Burgess et al. |
| 6,440,169 B1 | 8/2002 | Elberg et al. |

| | | |
|---|---|---|
| 6,524,310 B1 | 2/2003 | Lombardo et al. |
| 6,551,318 B1 | 4/2003 | Stahurski |
| 6,554,831 B1 | 4/2003 | Rivard et al. |
| 6,554,832 B2 | 4/2003 | Shluzas |
| 6,565,605 B2 | 5/2003 | Goble et al. |
| 6,579,319 B2 | 6/2003 | Goble et al. |
| 6,595,992 B1 * | 7/2003 | Wagner et al. ............... 606/250 |
| 6,602,253 B2 | 8/2003 | Richelsoph et al. |
| 6,610,091 B1 | 8/2003 | Reiley |
| 6,616,669 B2 | 9/2003 | Ogilvie et al. |
| 6,641,583 B2 | 11/2003 | Shluzas et al. |
| 6,645,207 B2 | 11/2003 | Dixon et al. |
| 6,669,729 B2 | 12/2003 | Chin |
| 6,673,073 B1 | 1/2004 | Schafer |
| 6,689,133 B2 | 2/2004 | Morrison et al. |
| 6,699,248 B2 * | 3/2004 | Jackson ....................... 606/300 |
| 6,702,814 B2 | 3/2004 | Walulik et al. |
| 6,736,817 B2 | 5/2004 | Troxell et al. |
| 6,752,807 B2 | 6/2004 | Lin et al. |
| 6,761,721 B2 | 7/2004 | Burgess et al. |
| 6,802,844 B2 | 10/2004 | Ferree |
| 6,811,567 B2 | 11/2004 | Reiley |
| 6,872,208 B1 | 3/2005 | McBride et al. |
| 6,875,211 B2 | 4/2005 | Nichols et al. |
| 6,887,241 B1 | 5/2005 | McBride et al. |
| 6,958,066 B2 | 10/2005 | Richelsoph et al. |
| 6,960,212 B2 | 11/2005 | Richelsoph et al. |
| 7,011,685 B2 | 3/2006 | Arnin et al. |
| 7,029,474 B2 | 4/2006 | Richelsoph et al. |
| 7,066,938 B2 | 6/2006 | Slivka et al. |
| 7,645,294 B2 | 1/2010 | Kalfas et al. |
| 7,717,939 B2 | 5/2010 | Ludwig et al. |
| 7,717,940 B2 | 5/2010 | Woods et al. |
| 7,879,074 B2 | 2/2011 | Kwak et al. |
| 7,967,845 B2 | 6/2011 | Lauryssen et al. |
| 8,192,471 B2 | 6/2012 | Ludwig et al. |
| 2002/0007183 A1 | 1/2002 | Lee et al. |
| 2002/0032442 A1 | 3/2002 | Altarac et al. |
| 2002/0052603 A1 | 5/2002 | Nichols et al. |
| 2002/0065557 A1 | 5/2002 | Goble et al. |
| 2002/0072800 A1 | 6/2002 | Goble et al. |
| 2002/0095154 A1 | 7/2002 | Atkinson et al. |
| 2002/0111625 A1 | 8/2002 | Richelsoph et al. |
| 2002/0123806 A1 | 9/2002 | Reiley |
| 2002/0133155 A1 | 9/2002 | Ferree |
| 2002/0138077 A1 | 9/2002 | Ferree |
| 2002/0143327 A1 | 10/2002 | Shluzas |
| 2002/0143330 A1 | 10/2002 | Shluzas |
| 2002/0151892 A1 | 10/2002 | Walulik et al. |
| 2002/0169448 A1 | 11/2002 | Vanacker |
| 2003/0004572 A1 | 1/2003 | Goble et al. |
| 2003/0018334 A1 | 1/2003 | Richelsoph et al. |
| 2003/0023244 A1 | 1/2003 | Richelsoph et al. |
| 2003/0028192 A1 | 2/2003 | Schar et al. |
| 2003/0028250 A1 | 2/2003 | Reiley et al. |
| 2003/0045874 A1 | 3/2003 | Thomas |
| 2003/0050640 A1 | 3/2003 | Lee et al. |
| 2003/0055427 A1 | 3/2003 | Graf |
| 2003/0083657 A1 | 5/2003 | Drewry et al. |
| 2003/0109880 A1 | 6/2003 | Shirado et al. |
| 2003/0114853 A1 | 6/2003 | Burgess et al. |
| 2003/0135277 A1 | 7/2003 | Bryan et al. |
| 2003/0153912 A1 | 8/2003 | Graf |
| 2003/0153914 A1 | 8/2003 | Oribe et al. |
| 2003/0153917 A1 | 8/2003 | Richelsoph et al. |
| 2003/0171749 A1 | 9/2003 | Le Couedic et al. |
| 2003/0171750 A1 | 9/2003 | Chin |
| 2003/0191470 A1 | 10/2003 | Ritland |
| 2003/0191532 A1 | 10/2003 | Goble et al. |
| 2003/0212398 A1 * | 11/2003 | Jackson ....................... 606/61 |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0006391 A1 | 1/2004 | Reiley |
| 2004/0039385 A1 | 2/2004 | Mazda et al. |
| 2004/0049188 A1 | 3/2004 | Slivka et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0087949 A1 | 5/2004 | Bono et al. |
| 2004/0111154 A1 | 6/2004 | Reiley |
| 2004/0116927 A1 | 6/2004 | Graf |
| 2004/0116928 A1 | 6/2004 | Young et al. |
| 2004/0127904 A1 | 7/2004 | Konieczynski et al. |
| 2004/0133203 A1 | 7/2004 | Young et al. |
| 2004/0143264 A1 | 7/2004 | McAfee |
| 2004/0167526 A1 | 8/2004 | Jackson |
| 2004/0172024 A1 | 9/2004 | Gorek |
| 2004/0176765 A1 | 9/2004 | Troxell et al. |
| 2004/0186474 A1 | 9/2004 | Matthis et al. |
| 2004/0186475 A1 | 9/2004 | Falahee |
| 2004/0236328 A1 | 11/2004 | Paul et al. |
| 2004/0236329 A1 | 11/2004 | Panjabi |
| 2004/0254574 A1 | 12/2004 | Morrison et al. |
| 2004/0260287 A1 | 12/2004 | Ferree |
| 2005/0010222 A1 | 1/2005 | Cordaro |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0080416 A1 | 4/2005 | Ryan et al. |
| 2005/0090821 A1 | 4/2005 | Berrevoets et al. |
| 2005/0090823 A1 | 4/2005 | Bartimus |
| 2005/0101954 A1 | 5/2005 | Simonson |
| 2005/0101956 A1 | 5/2005 | Simonson |
| 2005/0102028 A1 | 5/2005 | Arnin et al. |
| 2005/0113831 A1 | 5/2005 | Franck et al. |
| 2005/0113927 A1 | 5/2005 | Malek |
| 2005/0119657 A1 | 6/2005 | Goldsmith |
| 2005/0177152 A1 | 8/2005 | Baynham et al. |
| 2005/0192569 A1 | 9/2005 | Nichols et al. |
| 2005/0228326 A1 | 10/2005 | Kalfas et al. |
| 2005/0228376 A1 | 10/2005 | Boomer et al. |
| 2005/0228377 A1 | 10/2005 | Chao et al. |
| 2006/0058789 A1 | 3/2006 | Kim et al. |
| 2006/0058791 A1 | 3/2006 | Broman et al. |
| 2006/0064091 A1 | 3/2006 | Ludwig et al. |
| 2006/0142759 A1 | 6/2006 | Arnin et al. |
| 2006/0200130 A1 | 9/2006 | Hawkins et al. |
| 2006/0241757 A1 | 10/2006 | Anderson |
| 2006/0271045 A1 | 11/2006 | Hubbard et al. |
| 2006/0271051 A1 | 11/2006 | Berrevoets et al. |
| 2007/0043356 A1 | 2/2007 | Timm et al. |
| 2007/0049936 A1 | 3/2007 | Colleran et al. |
| 2007/0073289 A1 | 3/2007 | Kwak et al. |
| 2007/0073396 A1 | 3/2007 | Arnin |
| 2008/0109039 A1 | 5/2008 | Michielli et al. |
| 2010/0036420 A1 | 2/2010 | Kalfas et al. |
| 2010/0191289 A1 | 7/2010 | Ludwig et al. |

FOREIGN PATENT DOCUMENTS

| | | |
|---|---|---|
| DE | 3639810 | 5/1988 |
| DE | 4330837 | 3/1995 |
| EP | 0128058 | 12/1984 |
| EP | 0242708 | 10/1987 |
| EP | 0669109 | 8/1995 |
| EP | 0820722 | 1/1998 |
| EP | 0878170 | 11/1998 |
| EP | 0956829 | 11/1999 |
| EP | 1295566 | 3/2003 |
| FR | 2615095 | 11/1988 |
| FR | 2624720 | 6/1989 |
| FR | 2645427 | 10/1990 |
| FR | 2697743 | 5/1994 |
| FR | 2714590 | 7/1995 |
| FR | 2795622 | 1/2001 |
| FR | 2813782 | 3/2002 |
| FR | 2816195 | 5/2002 |
| GB | 167228 | 7/1921 |
| GB | 2173104 | 10/1986 |

| | | |
|---|---|---|
| GB | 2208476 | 4/1989 |
| JP | 11-244299 | 9/1999 |
| JP | 2000-033091 | 2/2000 |
| JP | 2004-073855 A | 3/2004 |
| RU | 1823791 | 6/1993 |
| SU | 286136 | 11/1970 |
| WO | 87/00160 | 1/1987 |
| WO | 90/04948 | 5/1990 |
| WO | 91/16020 | 10/1991 |
| WO | 95/13754 | 5/1995 |
| WO | 99/09903 | 3/1999 |
| WO | 9909903 | 3/1999 |
| WO | 00/57801 | 10/2000 |
| WO | 00/59387 | 10/2000 |
| WO | 01/01872 | 1/2001 |
| WO | 01/24718 | 4/2001 |
| WO | 01/45576 | 6/2001 |
| WO | 01/47425 A1 | 7/2001 |
| WO | 02/17803 | 3/2002 |
| WO | 02/30307 | 4/2002 |
| WO | 02/43603 | 6/2002 |
| WO | 02/102259 | 12/2002 |
| WO | 03/007828 | 1/2003 |
| WO | 03/009737 | 2/2003 |
| WO | 03063715 | 8/2003 |
| WO | 2004/024011 | 3/2004 |
| WO | 2004/034916 | 4/2004 |

OTHER PUBLICATIONS

"Ovation™ Polyaxial System" by Osteotech, Inc., description downloaded from http://www.osteotech.com/prodpoly2.htm; pp. 1-6.

Carson et al., "Internal Forces and Moments in Transpecular Spine Instrumentation", SPINE, vol. 15, No. 9, pp. 893-901 (1999).

Martin H. Krag, "Biomechanics of Thorocolumbar Spinal Fixation," SPINE, vol. 16, No. 3 Supplement, pp. S84-S99 (1991).

Lim, et al., "Biomechanics of Transfixation in Pedicle Screw Instrumentation", SPINE, vol. 21, No. 19, pp. 2224-2229, 1996.

Betz, Randall R. et al., DePuy AcroMed Brochure, "Fronterior Anterior Deformity System," Surgical Technique, 21 pages, Aug. 2002.

DePuy AcroMed, "CrossOver CrossConnector" brochure, Apr. 2003.

Dick et al., "Mechanical Evaluation of Cross-Link Designs in Rigid Pedicle Screw Systems", SPINE, vol. 22, No. 4, pp. 370-375, 1997.

Kaneda, Kiyoshi et al., DePuy AcroMed Brochure "Kaneda SR Anterior Spinal System," Surgical Technique, pp. 1-11, 1999.

DePuy AcroMed, "Modular Cross Connector (MCC)" brochure, 2000.

Hitodo, H., "Bone Fixing Device," Patent Abstracts of Japan; Sep. 14, 1999, No. 14; Abstract of JP 11244299.

Expedium SFX Cross Connector System Surgical Technique. Brochure, print date Nov. 2006.

Materials—Biocompatible non-fouling PEO coating for biomaterials, Biomedical Materials, International Newsletters, 1994, HighBeam Research, May 21, 2009 <http://www.highbeam.com>.

SFX Snap-Fit Cross Connector 510(k) Summary, approval date Sep. 11, 2006.

Office Action in Australian Pat. App. No. 2007318173 dated Apr. 21, 2010.

Office Action in Canadian Pat. App. No. 2,668,485 dated Nov. 8, 2010.

European Search Report EP 02257087.3 dated Feb. 19, 2003.

International Search Report from PCT/US2005/010513 dated Nov. 8, 2008, 5 pages.

International Search Report issued for PCT/US06/31000; mailing date Mar. 20, 2008, 4 pages.

International Search Report and Written Opinion in Pat. App. No. PCT/US07/22505 dated Jul. 11, 2008.

Japanese Office Action dated May 8, 2012 for Application No. 2007-506470.

Office Action dated Apr. 20, 2009 issued in U.S. Appl. No. 10/813,904.

* cited by examiner

DUAL ROD CROSS CONNECTORS AND INSERTER TOOLS

CROSS-REFERENCE TO RELATED APPLICATIONS

The present application is a continuation of U.S. patent application Ser. No. 10/929,095 filed Aug. 27, 2004 entitled "Dual Rod Cross Connectors And Inserter Tools," which is hereby incorporated by reference in its entirety.

FIELD OF THE INVENTION

The present invention relates to spinal fixation devices, and in particular to a cross connector for connecting spinal fixation elements, such as spinal fixation rods, implanted in a patient's spinal system, and to tools for implanting the same.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

Spinal cross connectors are often used in conjunction with spinal fixation devices to provide additional stability to the devices. For example, it has been found that when a pair of spinal rods are fastened in parallel on either side of the spinous process, the assembly can be significantly strengthened by using a cross connector to bridge the pair of spinal rods. The connectors are typically in the form of a rod having a clamp formed on each end thereof for mating with a spinal rod.

While current spinal cross connectors have proven effective, difficulties have been encountered in mounting the cross connectors, and maintaining them in a desired position and orientation with respect to the spinal rod, or other spinal fixation device to which they are attached. In particular, the clamp assemblies often consist of several parts which make surgical application tedious, and which can also increase the manufacturing costs. Since the cross connector is often applied as the last step in a lengthy surgical procedure, ease of application is paramount. Fixation of the cross connector to spinal rods can also be difficult where the rods are not parallel to one another, or they are diverging/converging with respect to one another.

Accordingly, there presently exists a need for an improved spinal cross connector that can be easily installed and that securely mates to and connects spinal fixation devices.

SUMMARY OF THE INVENTION

The present invention provides an implantable spinal cross connector for connecting spinal fixation devices, and more preferably for connecting two spinal fixation rods to one another. In one embodiment, an exemplary implantable spinal cross connector is provided having an elongate body with a central portion and opposed first and second ends. At least one rod-receiving recess is formed adjacent to at least one of the first and second opposed ends of the elongate body. The device also includes at least one rod-engaging member and a locking mechanism that is adapted to apply a force to the rod-engaging member(s) to cause it to move linearly to lock a spinal fixation rod within the at least one rod-receiving recess.

The configuration of the locking mechanism can vary, but in one exemplary embodiment, the central portion of the elongate body includes a central bore formed therein that is adapted to receive the locking mechanism. The locking mechanism can include a proximal portion that is adapted to engage a proximal portion of the central bore in the elongate body, and a distal shaft extending distally from the proximal portion. Preferably, the distal shaft is adapted to extend into the central bore to apply a force to the rod-engaging member(s) disposed within the elongate body to cause at least a portion of the rod-engaging member(s) to extend into the at least one rod-receiving recess to lock a spinal fixation rod therein. The distal shaft can optionally taper in a distal direction, and the rod-engaging member(s) can optionally include an internal surface that faces the central bore and that is substantially concave to seat the tapered shaft of the locking mechanism. In a further embodiment, the central bore can include threads formed therein for mating with corresponding threads formed on the proximal portion of the locking mechanism. The threads in the central bore and the threads on the proximal portion of the locking mechanism can optionally be sized to allow minor motion of the locking mechanism within the central bore.

The rod-engaging member(s) can also have a variety of configurations, but in an exemplary embodiment they are adapted to at least partially extend into the at least one rod-receiving recess to lock a spinal fixation element therein. More preferably, the rod-engaging member(s) is disposed within a rod-engaging member receiving cavity which extends between a central bore that is formed in the elongate body for receiving the locking mechanism, and the rod-receiving recess(es) in the elongate body. In an exemplary embodiment, the rod-engaging member(s) is slidably movable within the at least one receiving cavity. By way of non-limiting example, a pin member extending through the elongate body and into a groove formed within the rod-engaging member can be provided for slidably retaining each rod-engaging member within the receiving cavity. Each pin member is preferably effective to allow slidable movement of the rod-engaging members between a first retracted position in which the rod-engaging members are substantially positioned toward the central bore, and a second extended position in which the rod-engaging members are substantially positioned toward the rod-receiving recess.

In another exemplary embodiment of the present invention, an implantable spinal cross connector is provided and it includes an elongate body having a central portion and first and second rod-receiving recesses formed substantially adjacent to opposed terminal ends of the connector member. The elongate body can also include a first rod-engaging member extending between the central opening and the first rod-receiving recess, and a second rod-engaging member extending between the central opening and the second rod-receiving recess. The first and second rod-engaging members are preferably disposed within first and second cavities formed within the elongate body and extending between the central opening and the first and second rod-receiving recesses. The device also preferably includes a single locking mechanism that is matable to the central portion of the connector member and that is effective to lock first and second spinal fixation elements within the first and second rod-receiving recesses formed in the connector member. A central opening can be provided in the elongate body for receiving the locking mechanism.

In use, the rod-engaging members can be slidable between a first retracted position in which the rod-engaging members are substantially disposed within the first and second cavities in the elongate body, and a second extended position in which at least a portion of the rod-engaging members extend into the rod-receiving recesses formed within the elongate body. The locking mechanism is preferably effective to apply a force to the first and second rod-engaging members when the locking mechanism is disposed within the central opening to lock first and second spinal fixation elements within the first and second rod-receiving recesses.

In yet another embodiment of the present invention, an implantable spinal cross connector is provided having an elongate body with first and second rod-receiving recesses formed substantially adjacent to opposed first and second terminal ends therein, a first rod-engaging member that is adapted to extend into the first rod-receiving recess, a second rod-engaging member that is adapted to extend into the second rod-receiving recess. A locking mechanism is receivable within the elongate body and it is effective to apply a force to the first and second rod-engaging members to cause the first and second rod-engaging members to move linearly to lock a spinal fixation element within the first and second rod-receiving recesses.

The present invention also provides a method for connecting first and second spinal fixation rods that includes the steps of coupling first and second spinal fixation rods to one or more vertebrae in a patient's spinal column, positioning a spinal cross connector relative to the first and second spinal fixation rods such that the first spinal fixation rod is seated within a first rod-receiving recess in the spinal cross connector and the second spinal fixation rod is seated within a second rod-receiving recess in the spinal cross connector, and applying a single locking mechanism to the spinal cross connector to cause first and second rod-engaging members to move linearly to lock each of the first and second spinal fixation rods within the first and second rod-receiving recesses.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
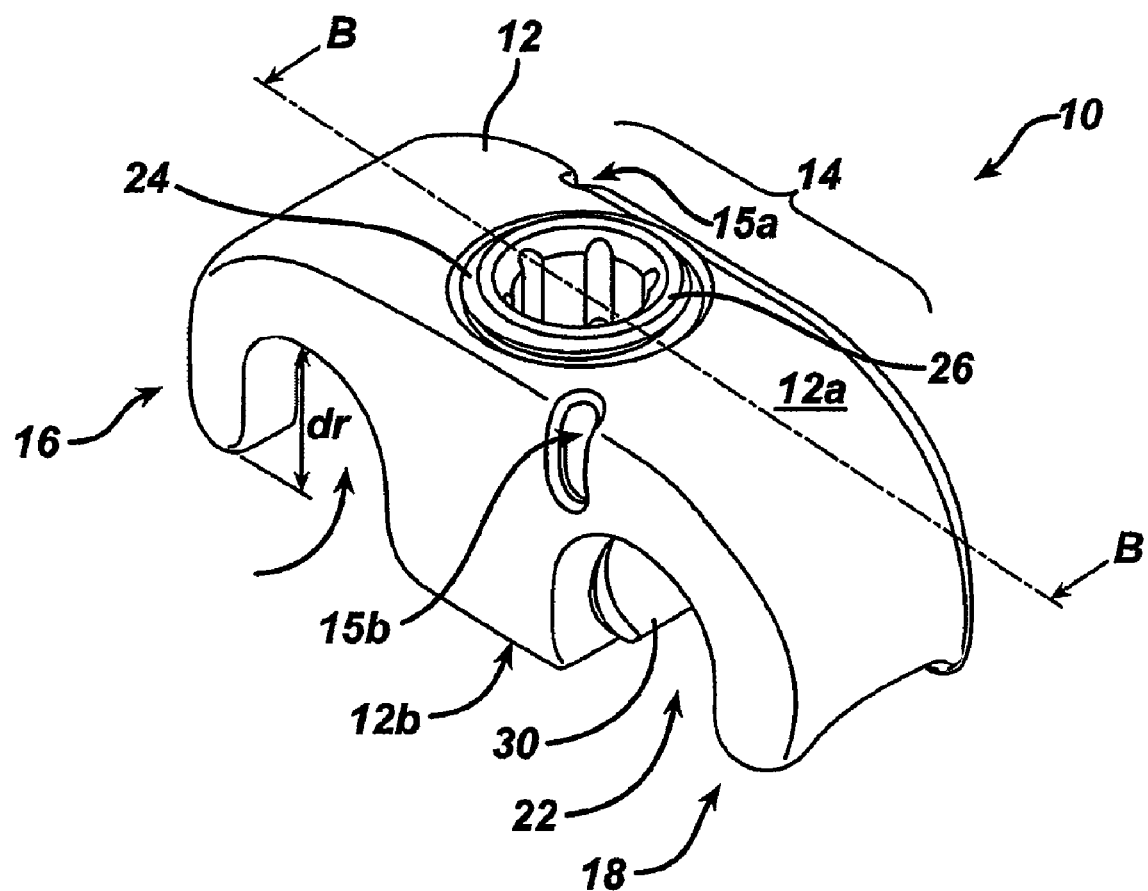
FIG. 1A is a side perspective view of one embodiment of a spinal cross connector according to the present invention.

The present invention provides a spinal cross connector for connecting one or more spinal fixation elements, and more preferably for connecting two spinal fixation rods, that are implanted within a patient's spinal system. In general, an exemplary cross connector in accordance with the present invention includes an elongate body with at least one rod-receiving recess formed therein, and a locking mechanism that is adapted to couple to the elongate body and that is effective to lock a spinal fixation rod within the rod-receiving recess(es).

A person skilled in the art will appreciate that while the cross connector 10 is described herein as being adapted to engage a spinal fixation element, and in particular a spinal fixation rod, that a cross connector of the present invention can be configured to engage a variety of spinal fixation elements, such as anchors, cables, fixation plates, etc. Moreover, the cross connector can include only one rod-receiving recess for engaging a spinal fixation element, and the opposed terminal end of the cross connector can be adapted for other uses. For example, the opposed terminal end of the cross connector can be configured to be fixedly attached to a vertebra or vertebral body replacement device or graft. The cross connectors of the present invention can also include any combination of features described and/or illustrated herein or known in the art, and the cross connector is not limited to the illustrated embodiments.

FIGS. 1A-1D illustrate one exemplary embodiment of a cross connector 10 in accordance with the present invention. As shown, the cross connector 10 has a generally elongate body 12. The configuration, shape, and size of the elongate body 12 can vary depending on the intended use, but preferably the elongate body 12 has a shape, size, and configuration that allows it to connect to and span two spinal fixation elements, such as spinal rods, that are implanted within a patient's spinal column. In an exemplary embodiment, the elongate body 12 includes a central portion 14 with opposed first and second terminal ends 16, 18. The length $L_b$ of the elongate body 12 extending between the opposed terminal ends 14, 16 will vary depending on the intended use. For example, the elongate body 12 can have a length $L_b$ that is in the range of about 10 mm to 30 mm for use in an anterior surgical approach. In an exemplary embodiment, the cross connector 10 is provided as part of a kit that includes multiple cross connectors having varying lengths $L_b$. The length $L_b$ of each cross connector 10 in the kit preferably differs in increments of about 1 mm.

As indicated above, the cross connector 10 is preferably adapted to connect to and span two spinal fixation elements, such as spinal rods, implanted within a patient's spinal column. Accordingly, the cross connector 10 can include one or more rod-receiving recesses formed therein. FIGS. 1A-1D illustrate first and second rod-receiving recesses 20, 22 formed therein and adapted to seat a spinal fixation rod. The location of the recesses 20, 22 can vary, but preferably the first and second rod-receiving recesses 20, 22 are formed substantially adjacent to the first and second terminals ends 16, 18 of the elongate body 12. As a result, when the cross connector 10 is connected to two spinal rods, the central portion 14 will extend between the rods. The rod-receiving recesses 20, 22 are also preferably formed in a bottom surface 12b of the elongate body 12 such that they are on an opposite side of the body 12 from a central opening 24 that is formed in the top surface 12a of the body 12 and which will be discussed in more detail below.

The rod-receiving recesses 20, 22 can vary in shape and size depending on the type of spinal fixation element being engaged. As previously noted, the cross connector 10 is preferably adapted to connect to two spinal fixation rods. Accordingly, each recess 20, 22 can have a shape that is configured to accommodate a substantially cylindrical spinal rod. In other words, each recess 20, 22 can be substantially concave such that it defines a partially cylindrical cavity. The size of the recesses 20, 22 can also vary depending on the size of the spinal fixation element. In an exemplary embodiment, each recess 20, 22 has a depth $d_r$ that is greater than a radius of the spinal fixation rod disposed therein. The depth $d_r$ can also be greater than a diameter of the spinal fixation rod, or is can be less than or substantially equal to a diameter of the spinal fixation rod. The recesses 20, 22 do, however, preferably seat a substantial portion of the spinal fixation rod to allow the rod to be firmly locked therein, as will be discussed in more detail below.

The cross connector 10 can also include one or more rod-engaging members, hereinafter referred to as shoes, that are configured to engage a spinal fixation element disposed within the recesses 20, 22. As shown in FIGS. 1A-1D, the cross connector 10 includes first and second shoes 28, 30 that are slidably disposed within the elongate body 12 adjacent to the first and second rod-receiving recesses 20, 22. The shoes 28, 30 can have a variety of configurations and they can be mated to or disposed within the elongate body 12 using a variety of techniques, but they are preferably effective to move linearly in response to a force applied thereto by the locking mechanism 26 to lock a spinal fixation rod within each rod-receiving recess 20, 22. In an exemplary embodiment, the elongate body 12 includes first and second receiving cavities 32, 34 formed therein for slidably seating the shoes 28, 30. The first and second cavities 32, 34 preferably extend between the central opening 24 formed in the central portion 14 of the elongate body 12, and the first and second rod-receiving recesses 20, 22 in the body 12. The cavities 32, 34 are also preferably spaced a distance apart from the bottom surface 12b of the elongate body 12 to allow the shoes 28, 30 to be retained within the body 12.

Each cavity 32, 34 can vary in shape and size, but they should allow slidable movement of the shoes 20, 22 therein. More preferably, each cavity 32, 34 has a shape that is substantially similar to a shape of the shoes 20, 22. In the illustrated embodiment, each cavity 32, 34 has a substantially elongate rectangular shape that is configured to match the contour of each shoe 28, 30, as will be discussed below. The cavities 32, 34 can also extend at a downward angle from the central bore 24 toward the rod-receiving recesses 20, 22 such that each shoe 28, 30, when moved from within the cavity 32, 34 toward the rod-receiving recess 20, 22, extends in a downward direction. Such a configuration facilitates engagement of the rods disposed within the rod-receiving recesses 20, 22.

Figure 1B:
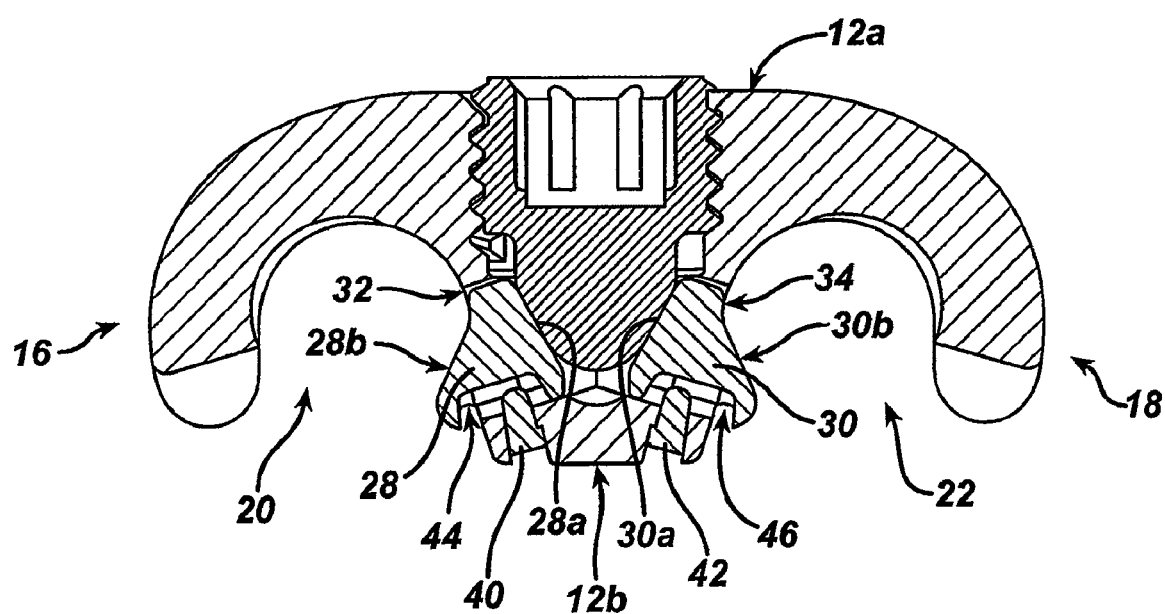
FIG. 1B is a cross-sectional view of the spinal cross connector shown in FIG. 1A taken along line B-B.
Figure 1C:
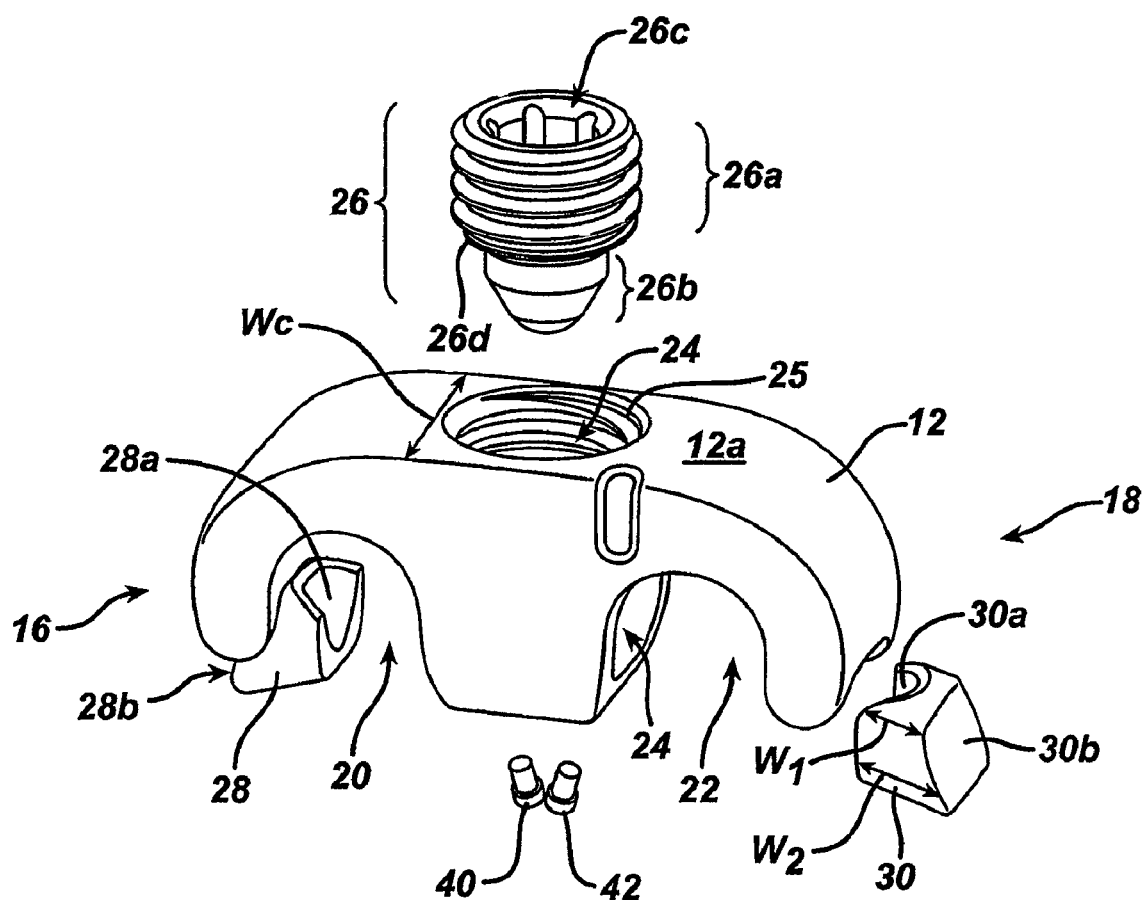
FIG. 1C is a disassembled view of the spinal cross connector shown in FIG. 1A.

The shoes 28, 30 are shown in more detail in FIGS. 1B and 1C, and as shown each shoe 28, 30 can have a generally rectangular or square cross-sectional shape taken along a plane that extends between an internal surface 28a, 30a and an external surface 28b, 30b thereof. The internal surface 28a, 30a faces the central opening 24 when the shoe 28, 30 is disposed within the cavity 32, 34, and the opposed external surface 28b, 30b faces the rod-receiving recess 20, 22. While the cross-section of the shoes 28, 30 can be substantially square or rectangular, the internal and external surfaces 28a, 30a, 38b, 30b can vary in shape. In particular, the internal surface 28a, 30a of each shoe 28, 30 can have a shape that conforms to the shape of the locking mechanism 26, which will be discussed in more detail below. In an exemplary embodiment, the internal surface 28a, 30a of each shoe 28, 30 includes a concave recess formed therein, as shown. The concave shape of the internal surface 28a, 30a is effective to seat a portion of the locking mechanism 26. As is further shown in FIG. 1C, the external surface 28b, 30b of each shoe 28, can have a substantially planar configuration, but each surface 28b, 30b can extend at an angle such that a width $w_1$ at a top portion of each shoe 28, 30 is less than a width $w_2$ at a bottom portion of each shoe 28, 30. In other words, the width of each shoe 28, 30 decreases from the top to the bottom. This configuration allows only a mid-portion or the bottom portion of each shoe 28, 30 to come into contact with a spinal fixation rod disposed within the rod-receiving recess 20, 22 in the elongate body 12 when the shoes 28, 30 are in a locked configuration as a result of the locking mechanism 26. The external surface 28b, 30b of each shoe 28, 30 can also be optimizing to facilitate engagement of a spinal fixation rod. By way of non-limiting example, the surfaces 28b, 30b, or at least a portion thereof, can include gripping features, such as ridges, grooves, a surface coating, etc., formed or disposed thereon to engage the rod.

In use, the first and second shoes 28, 30 are preferably slidably movable between a first retracted position (not shown) in which the shoes 28, 30 are at least partially or fully disposed within the first and second cavities 32, 34 in the elongate body 12, and a second extended position, as shown in FIGS. 1A and 1B, in which at least a portion of the shoes 28, 30 extend into the recesses 20, 22 formed within the elongate body 12. In the first retracted position, at least a portion of the shoes 28, 30 can extend into the central opening 24 in the elongate body 12. The shoes 28, 30 can be moved into the second extended position by inserting the locking mechanism 26 into the opening 24 such that the locking mechanism 26 applies a force to the first and second movable shoes 28, 30 to cause the shoes 28, 30 to move linearly and lock first and second spinal fixation rods within the first and second rod-receiving recesses 20, 22.

In order to prevent the shoes 28, 30 from falling out of the cavities during movement, the device 10 can include a mechanism to slidably retain each shoe 28, 30 within each cavity 32, 34. While various techniques can be used, in one exemplary embodiment, as shown, the cross connector 10 includes first and second pin members 40, 42 that extend through the bottom surface 12b of the body 12 and into a groove 44, 46 formed within a bottom surface of each shoe 28, 30. The groove 44, 46 preferably extends between the internal and external faces 28a, 30a, 38b, 30b of the shoes 28, 30 to allow the shoes 28, 30 to slide between the retracted and extended positions. The pin members 40, 42 can be retained within the elongate body 12 using various techniques, but preferably the pin members 40, 42 are fixedly mated to the elongate body 12 using a press fit or using other techniques known in the art.

Figure 4A:
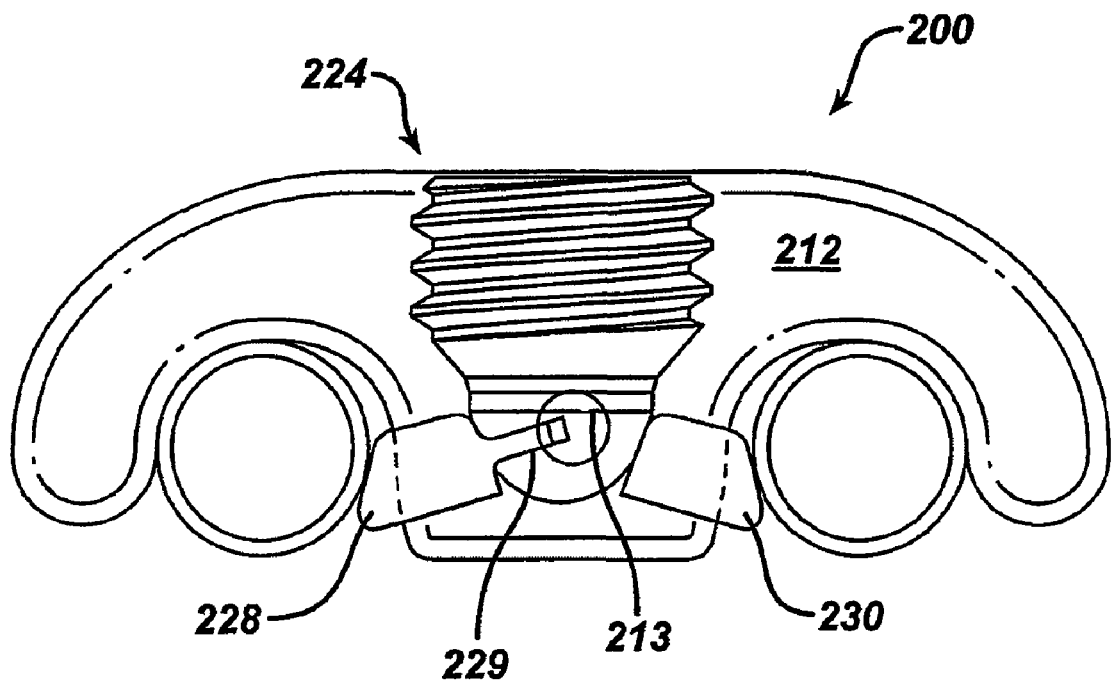
FIG. 4A is a side, partially cross-sectional view of another embodiment of a spinal cross connector in accordance with the present invention.
Figure 4B:
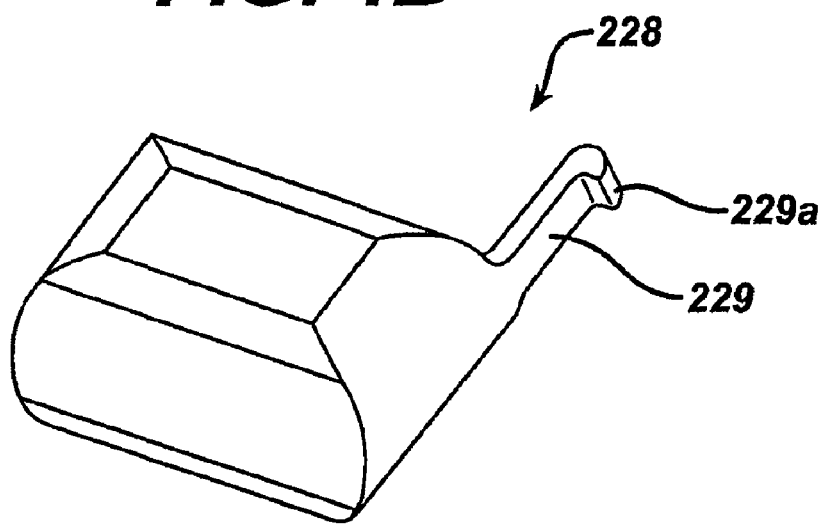
FIG. 4B is an enlarged perspective view of one of the rod-engaging members of the cross connector shown in FIG. 4A.
Figure 5:
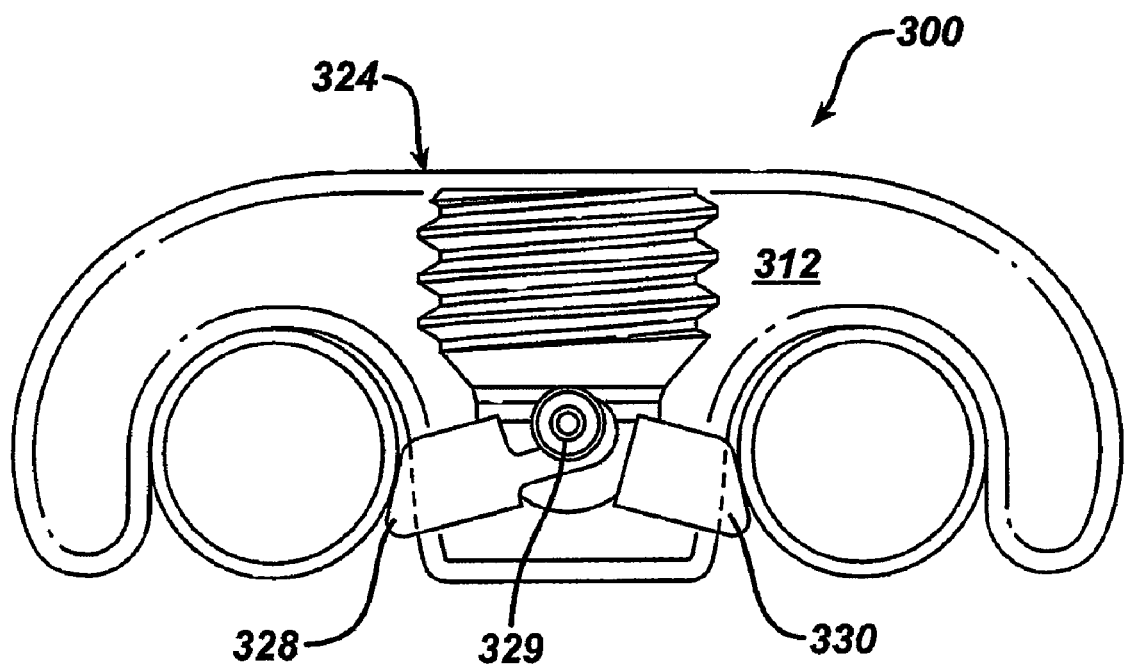
FIG. 5 is a side, partially cross-sectional view of yet another embodiment of a spinal cross connector in accordance with the present invention.

Other embodiments of techniques for retaining the shoes within the connector body are shown in FIGS. 4A-5. FIG. 4A illustrates a connector 200 that is similar to connector 10 and that includes connector body 212 with shoes 228 and 230 disposed therein. In this embodiment, each shoe 228, 230 includes a tab that extends toward the central opening 224 of the connector body 212, and that includes a protrusion formed thereon that is adapted to extend into a bore or groove formed in the connector body 212. The tabs on the shoes 228, 230 are preferably formed on opposite sides of the connector body 212, thus FIG. 4A only illustrates tab 229 formed on shoe 228. The protrusion 229a on tab 229 is shown in detail in FIG. 4B. In use, the protrusion 229a on the tab 229 extends into a bore 213 formed in a sidewall of the connector body 212. The tab 229 is preferably deflectable to allow the shoe 228 to be snapped into the connector body 212. Once the protrusion 229a on the tab 229 is in engagement with the bore 213, the protrusion 229a is free to move within the bore 213, thus allowing the shoe 228 to slidably move relative to the connector body 212.

In the embodiment shown in FIG. 5, the shoes 328, 330 are retained within the body 312 of the connector 300 by a hook-type engagement. In particular, each shoe 328, 330 preferably includes a hook member that extends toward the central opening 324 in the body 312. The hook members on the shoes 328, 330 are preferably formed on opposite sides of the connector body 312, thus FIG. 5 only illustrates hook member 329 formed on shoe 328. Thus, referring to shoe 328, the hook member 329 is configured to engage a pin 313 that protrudes into the central opening 324 formed in the connector body 312 such that the hook member 329 extends around the pin 313. In use, the length of the hook member 329 allows the shoe 328 to slidably move relative to the connector body 312 while the pin 313 prevents the hook member 329, and thus the shoe 328, from falling out of the connector body 312. A person skilled in the art will appreciate that a variety of other techniques can be used to retain the shoes within the connector body.

As noted above, the device 10 further includes a locking mechanism 26 that is adapted to apply a force to the shoes 28, 30 to linearly move the shoes 28, 30 from the first retracted position to the second extended position. The locking mechanism 26 can have a variety of configurations and it can be receivable within the elongate body 12 at a variety of locations. In one exemplary embodiment, as shown in FIGS. 1A-1D, the elongate body 12 includes a central opening 24 formed in a top surface 12a thereof for receiving the locking mechanism 26. The central opening 24 can extend completely through the elongate body 12, but it preferably terminates at a location that is a distance apart from the bottom surface 12b of the body 12. The locking mechanism 26, which is receivable within the opening 24, can include a proximal portion 26a that is adapted to mate to a proximal portion of the central opening 24, and a distal portion 26b that is adapted to apply a force to the shoes 28, 30 to move the shoes 28, 30 into the second extended position. While various techniques can be used to mate the locking mechanism 26 to the central opening 24, in the illustrated embodiment the proximal portion 26a of the locking mechanism 26 includes threads 26d formed thereon for mating with corresponding threads 25 formed within at least a proximal portion of the central opening 24. The distal portion 26b of the locking mechanism 26 can also vary in shape and size, but in one exemplary embodiment the distal portion 26b of the locking mechanism 26 is in the form of a shaft or pin-type member. At least a portion of the shaft 26b preferably tapers toward the distal end to facilitate the application of force against the shoes 28, 30. In particular, as previously indicated, the internal surface 28a, 30a of each shoe 28, 30 can have a concave recess formed therein for seating the tapered shaft 26b. Thus, when the locking mechanism 26 is threaded into the central opening 24, the tapered shaft 26b contacts the concave internal surface 28a, 30a of each shoe 28, to force the shoes 28, 30 into the second extended position. The shaft 26b can also have a variety of other shapes such as, for example, a spherical shape or cone shape. A person skilled in the art will appreciate that the shape of the distal portion 26b of the locking mechanism 26 can vary depending on the shape of the shoes 28, 30.

Figure 1D:
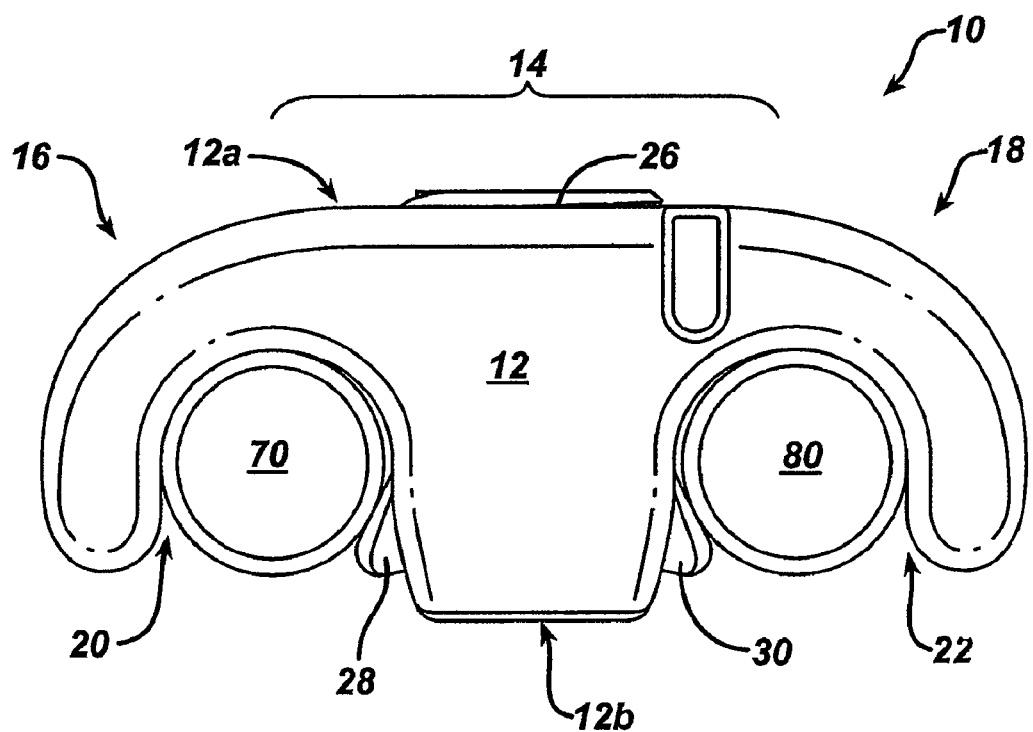
FIG. 1D is a side view of the spinal cross connector shown in FIG. 1A having first and second spinal fixation rods disposed and engaged therein.

In use, the cross connector 10 can be coupled to one or more, and preferably two, spinal fixation elements, such as spinal rods, that are implanted within a patient's spine, as shown in FIG. 1D. This can be achieved by positioning the cross connector 10 such that a spinal rod 70, 80 is seated within each rod-receiving recess 20, 22. In this position, the shoes 28, 30 are in the first retracted position, as the locking mechanism 26 is not yet inserted into the central opening 24, or it is only loosely threaded in the central opening 24. The spinal rods 70, 80 may also force the shoes 28, 30 into the retracted position. Once the cross connector 10 is properly disposed over the spinal rods 70, 80, the locking mechanism 26 can then be threaded into the central opening 24. As the locking mechanism 26 is rotated, the distal shaft 26b will contact the internal surface 28a, 30a of the shoes 28, 30 to push the shoes 28, 30 toward the rod-receiving recesses 20, 22, thereby pushing the shoes 28, 30 against the spinal rods 70, 80 disposed therein. The locking mechanism 26 is threaded until the shoes 28, 30 lock the rods 70, 80 into the recesses 20, 22, as shown in FIG. 1D. The threads 26d on the locking mechanism 26 and the threads 25 in the central opening 24 can optionally be designed such that, when the locking mechanism 26 is fully threaded into the central opening 24, the shoes 28, 30 are in a locked position. The threads 26d, 25 can also be designed to allow some minor movement between the locking mechanism 26 and the elongate body 12 to allow for any imbalance between the position of the shoes 28, 30. Imbalances can occur as a result of the position of the spinal rods implanted in the patient's spine, e.g., when the rods are not parallel to one another. In an exemplary embodiment, a minor gap can be provided between the threads 25 in the central opening such that the locking mechanism 26 can slightly move side-to-side when disposed therein. A person skilled in the art will appreciate that a variety of other techniques can be used to facilitate the equal distribution of force by the locking mechanism 26 onto the shoes 28, 30 such that the shoes 28, 30.

Figure 2:
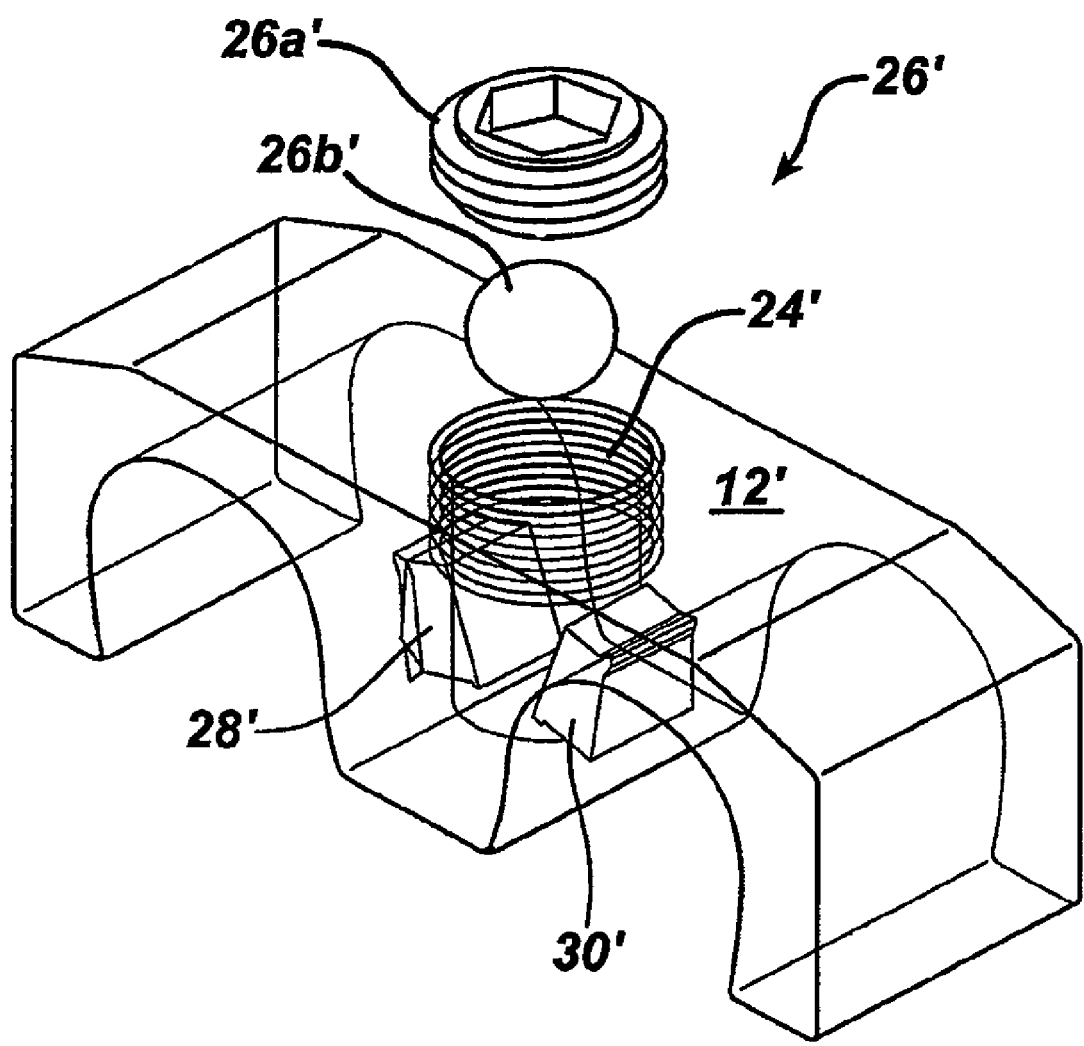
FIG. 2 is a transparent side perspective view of yet another embodiment of a spinal cross connector in a disassembled state.

The locking mechanism 26 can have a variety of other configurations, and a variety of other techniques can be used to move the shoes 28, 30 between the first retracted position and the second extended position, and to lock the shoes in a fixed position to engage spinal fixation elements disposed within the recesses 20, 22. By way of non-limiting example, FIG. 2 illustrates another embodiment of a locking mechanism 26' that includes two separate components: a ball-type member 26b' and a threaded member 26a'. The ball-type member 26b' sits within the central opening 24' in the elongate body 12', and the threaded member 26a' can be threaded into the opening 24' to push the ball-type member 26b' downward, thereby moving the shoes 28', 30' into the extended position.

Figure 3A:
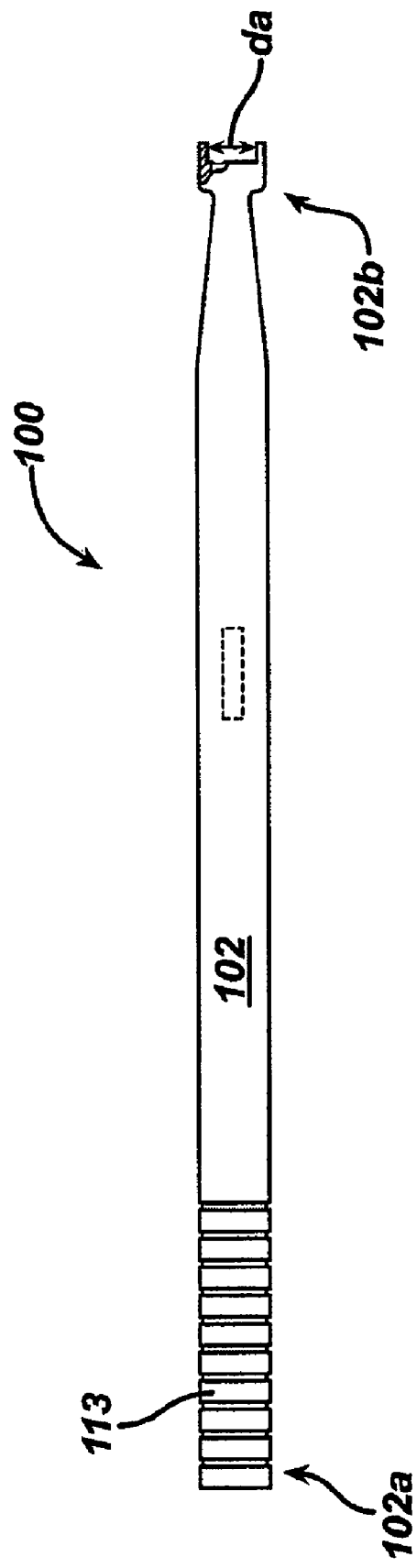
FIG. 3A is a perspective view of one embodiment of an insertion tool for use with the spinal cross connector shown in FIG. 1A.
Figure 3B:
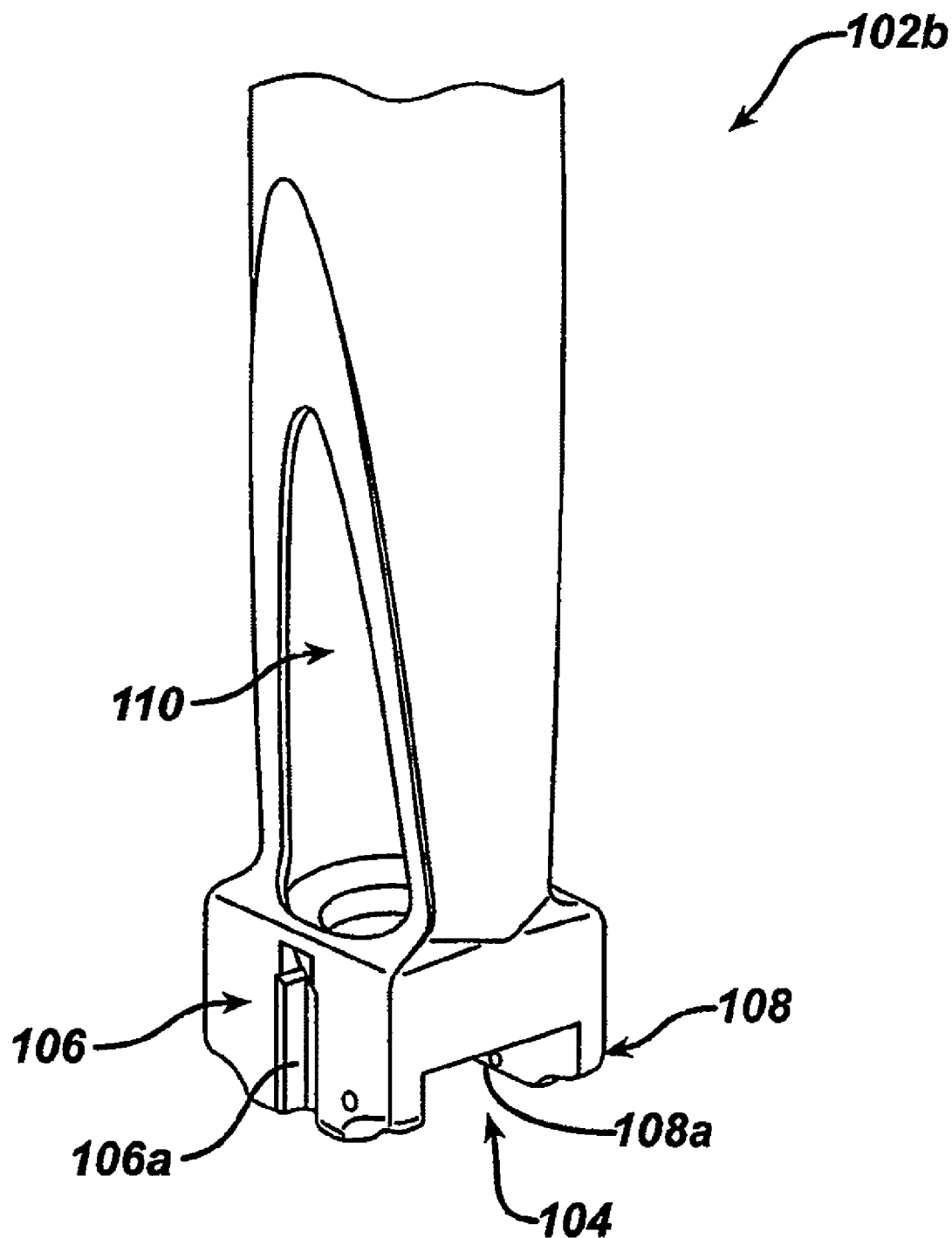
FIG. 3B is an enlarged view of the distal portion of the insertion tool shown in FIG. 3A.

The present invention also provides an inserter tool 100 that can be used to position a spinal implant or device with respect to one or more spinal fixation elements, such as two spinal rods. While the tool 100 is described for use with cross connector 10, the tool can be used with a variety of spinal implants and devices. Referring to FIGS. 3A-3B, one exemplary embodiment of an inserter tool 100 is shown in accordance with the present invention. In general, the tool 100 includes an elongate shaft 102 having a proximal handle end 102a and a distal end 102b. The elongate shaft 102 is preferably hollow to allow other tools, such as a driver for rotating the locking mechanism 26, to be inserted therethrough. The proximal handle end 102a can have a variety of configurations, shapes, and sizes, but it is preferably adapted to allow a user to easily grasp the tool 100. As shown in FIG. 3A, the handle 102a includes ridges 103 formed thereon to facilitate grasping of the device 100. The distal end 102b of the elongate shaft 102 is configured to grasp the cross connector 10 to position the cross connector 10 in relation to one or more spinal fixation elements implanted in a patient's spine.

The distal end 102b of the elongate shaft 102 of the inserter tool 100 is shown in more detail in FIG. 3B, and as shown the distal end 102b includes first and second arms 106, 108 which are effective to engage the central portion 14 of the cross connector 10. The arms 106, 108 preferably define a cavity 104 therebetween that has a shape that generally corresponds to the contour of the central portion 14 of the cross connector 10. In particular, the cavity 104 can be substantially square or rectangular in shape to receive the central portion 14. The distal end 102b of the inserter tool 100 can also have a substantially square or rectangular shape to define the shape of the cavity 104 as well as the position of the arms 106, 108 relative to one another.

Each arm 106, 108 of the inserter tool 100 can also be flexible, or include a flexible portion, to create a friction fit between the arms 106, 108 and the central portion 14 of the cross connector, thereby allowing the cross connector 10 to be removably mated to the inserter tool 100. As shown in FIG. 3B, arm 106 has a flexible tab 106a formed at a substantial mid-portion thereof. While only partially shown, arm 108 can also include a flexible tab 108a formed thereon. The flexible tabs 106a, 108a can have any shape and size, but they preferably define a distance $d_a$ (FIG. 3A) therebetween that is equal to or slightly less than a width $w_c$ (FIG. 1C) of the central portion 14 of the cross connector 10.

The arms 106, 108 of the inserter tool 100 can also include one or more features formed thereon for aligning the tool 100 with the cross connector 10. By way of non-limiting example, an inner surface of each arm 106, 108 can include a protrusion (not shown) formed thereon for fitting within a corresponding detent or groove formed on the central portion 14 of the cross connector. In an exemplary embodiment, the protrusions are formed on diagonally opposed ends of the opposed arms 106, 108, and the grooves 15a, 15b are formed on diagonally opposed sides of the central portion 14 of the cross connector 10, as shown in FIG. 1A. This allows the inserter tool 100 to be properly aligned with the cross connector 10, and in particular such a feature is effective to align the lumen extending through the inserter tool 100 with the central opening 24 formed in the cross connector 10.

The inserter tool 100 can also optionally include one or more cut-out portions or windows formed therein to facilitate viewing of the central opening 24 in the cross connector 10 when the cross connector 10 is coupled to the tool 100. By way of non-limiting example, FIG. 3B illustrates window 110 formed in the shaft 102 of the inserter tool 100 just proximal to the distal end 102b. While not shown, a second window can be formed opposed to the first window 110.

The present invention also provides a method for coupling to spinal fixation elements, such as spinal rods, implanted within a patient's spinal column. In general, as previously described with respect to FIG. 1C, after the spinal fixation rods 70, 80 are implanted using techniques know in the art, the rods 70, 80 can be rigidly coupled to one another by positioning the cross connector 10 over the rods 70, 80 such that the rods 70, 80 sit within the recesses 20, 22 in the cross connector 10. The inserter tool 100 can be used to facilitate such positioning of the cross connector 10. In particular, the cross connector 10 can be positioned between and engaged by the opposed arms 106, 108 of the inserter tool 100. The tool 100 can then be manipulated to position the cross connector 10 over the rods 70, 80. A driver mechanism (not shown) can then be inserted through the hollow elongate shaft 102 of the inserter tool 100 to rotate the locking mechanism 26, which is preferably loosely pre-threaded into the central opening 24, thereby moving the shoes 28, 30 to lock the spinal rods 70, 80 relative to the cross connector 10.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable spinal cross connector, comprising:
   an elongate body having an opening and first and second rod-receiving recesses formed therein;
   a first cavity formed in the elongate body and extending between the opening and the first rod-receiving recess;
   a second cavity formed in the elongate body and extending between the opening and the second rod-receiving recess;
   a first rod-engaging member linearly slidably disposed within the first cavity;
   a second rod-engaging member linearly slidably disposed within the second cavity; and
   a locking mechanism configured to be received in the opening and to simultaneously linearly slide the first and second rod-engaging members in opposed directions in the first and second cavities to lock first and second spinal fixation rods within the first and second rod-receiving recesses.

2. The implantable spinal cross connector of claim 1, wherein a bottom portion of the first and second rod-engaging members has a width that is greater than a width of a top portion of the first and second rod-engaging members.

3. The implantable spinal cross connector of claim 1, wherein the locking mechanism includes a proximal, threaded portion configured to engage the opening and a distal, non-threaded portion configured to engage the first and second rod-engaging members.

4. The implantable spinal cross connector of claim 3, wherein the distal portion of the locking mechanism tapers in a distal direction.

5. The implantable spinal cross connector of claim 4, wherein a surface of the first and second rod-engaging members that faces the opening is substantially concave to seat the tapered distal portion of the locking mechanism.

6. The implantable spinal cross connector of claim 1, further comprising first and second pin members extending through the elongate body and into grooves formed in the first and second rod-engaging members to slidably retain the first and second rod-engaging members within the first and second cavities.

7. The implantable spinal cross connector of claim 1, wherein the first and second cavities extend at a downward angle from the opening toward the first and second rod-receiving recesses.

8. An implantable spinal cross connector, comprising:
   an elongate body having an opening, first and second cavities, and first and second rod-receiving recesses formed therein;
   first and second rod-engaging members linearly slidably disposed within the first and second cavities; and
   a locking mechanism configured to be received in the opening of the elongate body and to simultaneously engage a first external surface of the first rod-engaging member and a first external surface of the second rod-engaging member to slidably move the first and second rod-engaging members in opposed directions in the first and second cavities to lock first and second spinal fixation rods within the first and second rod-receiving recesses.

9. The implantable spinal cross connector of claim 8, wherein the first cavity extends between the opening and the first rod-receiving recess and the second cavity extends between the opening and the second rod-receiving recess.

10. The implantable spinal cross connector of claim 8, wherein the first cavity extends at a downward angle from the opening toward the first rod-receiving recess and the second cavity extends at a downward angle from the opening toward the second rod-receiving recess.

11. The implantable spinal cross connector of claim 8, wherein the first rod-engaging member has a first external surface facing the opening and a second external surface facing the first rod-receiving recess and the second rod-engaging member has a first external surface facing the opening and a second external surface facing the second rod-receiving recess.

12. The implantable spinal cross connector of claim 11, wherein the first external surface of the first rod-engaging member and the first external surface of the second rod-engaging member are substantially concave.

13. The implantable spinal cross connector of claim 12, wherein the locking mechanism has a tapered portion configured to engage the first external surfaces of the first and second rod-engaging members and to apply a force to the first and second rod-engaging members to lock the first and second spinal fixation rods within the first and second rod-receiving recesses.

14. The implantable spinal cross connector of claim 11, wherein the second external surface of the first rod-engaging member and the second external surface of the second rod-engaging member are substantially planar.

15. The implantable spinal cross connector of claim 14, wherein the second external surface of each rod-engaging member extends at an angle such that a bottom portion of the rod-engaging member has a width that is greater than a width of a top portion of the rod-engaging member.

16. The implantable spinal cross connector of claim 8, wherein the first rod-engaging member includes a gripping feature configured to engage the first spinal fixation rod within the first rod-receiving recess and the second rod-engaging member includes a gripping feature configured to engage the second spinal fixation rod within the second rod-receiving recess.

17. An implantable spinal cross connector, comprising:
an elongate body having an opening and a rod-receiving recess formed therein, the opening having a central axis that is perpendicular to a longitudinal axis of the body;
a rod-engaging member linearly slidably disposed within the elongate body; and
a locking mechanism configured to be received in the opening and to apply a force to the rod-engaging member to linearly slide the rod-engaging member from a first position in which the rod-engaging member is at least partially retracted into the elongate body and a second position in which the rod-engaging member extends from the elongate body to engage and lock a spinal fixation rod within the rod-receiving recess.

18. The implantable spinal cross connector of claim 17, further comprising a cavity formed in the elongate body and extending between the opening and the rod-receiving recess for retaining the rod-engaging member.

19. The implantable spinal cross connector of claim 18, wherein the cavity extends at a downward angle from the opening toward the rod-receiving recess.

20. The implantable spinal cross connector of claim 17, wherein the locking mechanism includes a proximal, threaded portion configured to engage the opening and a distal, non-threaded portion configured to engage the rod-engaging member.

21. The implantable spinal cross connector of claim 17, further comprising a pin member extending through the elongate body and into a groove formed in the rod-engaging member to slidably retain the rod-engaging member within the elongate body.

22. The implantable spinal cross connector of claim 21, wherein the pin member is effective to allow slidable movement of the rod-engaging member between the first position and the second position.

* * * * *